(12) United States Patent
Gustafson et al.

(10) Patent No.: US 12,150,640 B2
(45) Date of Patent: Nov. 26, 2024

(54) METHODS AND SYSTEMS FOR KNOTLESS SUTURE ANCHORING

(71) Applicant: Medos International Sarl, Le Locle (CH)

(72) Inventors: Adam Gustafson, Dighton, MA (US); Gerome Miller, Randolph, MA (US); Benjamin Cleveland, Weymouth, MA (US); Stefan Gabriel, Mattapoisett, MA (US)

(73) Assignee: Medos International Sarl, Le Locle (CH)

( * ) Notice: Subject to any disclaimer, the term of this patent is extended or adjusted under 35 U.S.C. 154(b) by 615 days.

(21) Appl. No.: 17/479,119

(22) Filed: Sep. 20, 2021

(65) Prior Publication Data

US 2022/0039790 A1  Feb. 10, 2022

Related U.S. Application Data

(60) Continuation of application No. 16/281,549, filed on Feb. 21, 2019, now Pat. No. 11,123,060, which is a
(Continued)

(51) Int. Cl.
*A61B 17/04* (2006.01)

(52) U.S. Cl.
CPC ...... *A61B 17/0401* (2013.01); *A61B 17/0485* (2013.01); *A61B 2017/0403* (2013.01);
(Continued)

(58) Field of Classification Search
CPC ........ A61B 17/0401; A61B 2017/0409; A61B 2017/0414; A61B 2017/042;
(Continued)

(56) References Cited

U.S. PATENT DOCUMENTS

| 5,649,963 A | 7/1997 | McDevitt |
| 5,906,632 A | 5/1999 | Bolton |

(Continued)

FOREIGN PATENT DOCUMENTS

| CN | 104042264 A | 9/2014 |
| EP | 2238914 A1 | 10/2010 |

(Continued)

OTHER PUBLICATIONS

U.S. Appl. No. 15/457,944, filed Mar. 13, 2017, Gerome Miller et al.
(Continued)

*Primary Examiner* — Dianne Dornbusch
(74) *Attorney, Agent, or Firm* — Mintz Levin Cohn Ferris Glovsky and Popeo, P.C.

(57) ABSTRACT

Methods and systems are provided for securing tissue to bone. A surgical system can include an outer shaft, an elongate inner shaft, and an implantable suture anchor assembly including first and second anchor bodies. The second, more proximal, anchor body has one or more openings extending through a side wall or through opposed side walls thereof. The inner shaft is configured to be received within the outer shaft and through the first and second anchor bodies such that a distal end of the inner shaft protrudes beyond a distal end of the first anchor body. The inner shaft is configured to be removably coupled to the first anchor body such that the inner shaft is configured to be rotated to cause a proximal portion of the first anchor body to move proximally into a lumen extending through the second anchor body and to occlude the opening in the second anchor body.

13 Claims, 12 Drawing Sheets

Related U.S. Application Data division of application No. 15/458,007, filed on Mar. 13, 2017, now Pat. No. 10,245,020.

(52) U.S. Cl.
CPC ............ *A61B 2017/0409* (2013.01); *A61B 2017/0412* (2013.01); *A61B 2017/0414* (2013.01); *A61B 2017/0427* (2013.01); *A61B 2017/0441* (2013.01); *A61B 2017/0445* (2013.01); *A61B 2017/0453* (2013.01); *A61B 2017/0458* (2013.01); *A61B 2017/0464* (2013.01)

(58) Field of Classification Search
CPC .... A61B 2017/0422; A61B 2017/0424; A61B 2017/0425; A61B 2017/0427; A61B 2017/0429; A61B 2017/043; A61B 2017/0433; A61B 2017/0435; A61B 2017/044; A61B 2017/0445; A61B 2017/0446; A61B 2017/0448; A61B 2017/045; A61B 2017/0451; A61B 2017/0453; A61B 2017/0454; A61B 2017/0456; A61B 2017/0458; A61B 2017/0459; A61F 2/0811; A61F 2002/0835; A61F 2002/0888; A61F 2002/0858; A61F 2002/0829; A61F 2002/0817; A61F 2002/0823

See application file for complete search history.

(56) References Cited

U.S. PATENT DOCUMENTS

| | | | |
|---|---|---|---|
| 6,319,252 B1 * | 11/2001 | McDevitt | A61B 17/0401 606/60 |
| 6,527,794 B1 | 3/2003 | McDevitt et al. | |
| 6,673,094 B1 * | 1/2004 | McDevitt | A61B 17/0401 606/232 |
| 7,780,701 B1 | 8/2010 | Meridew et al. | |
| 7,993,369 B2 | 8/2011 | Dreyfuss | |
| 8,202,295 B2 | 6/2012 | Kaplan | |
| 8,469,998 B2 | 6/2013 | Sojka et al. | |
| 8,523,902 B2 | 9/2013 | Heaven et al. | |
| 8,535,350 B2 | 9/2013 | Lizardi et al. | |
| 8,974,494 B2 | 3/2015 | Paulk et al. | |
| 9,265,601 B2 | 2/2016 | Bojarski et al. | |
| 9,277,910 B2 | 3/2016 | Nason et al. | |
| 9,295,460 B2 | 3/2016 | Hoof et al. | |
| 9,510,820 B2 | 12/2016 | Hernandez et al. | |
| 9,737,293 B2 | 8/2017 | Sengun et al. | |
| 10,245,020 B2 | 4/2019 | Gustafson et al. | |
| 10,368,857 B2 | 8/2019 | Miller et al. | |
| 11,123,060 B2 | 9/2021 | Gustafson et al. | |
| 11,141,146 B2 | 10/2021 | Miller et al. | |
| 2002/0111653 A1 | 8/2002 | Foerster | |
| 2003/0125749 A1 * | 7/2003 | Yuan | A61B 17/8875 606/104 |
| 2005/0283158 A1 | 12/2005 | West | |
| 2007/0005068 A1 | 1/2007 | Sklar | |
| 2009/0292321 A1 | 11/2009 | Collette | |
| 2011/0112576 A1 | 5/2011 | Nguyen et al. | |
| 2011/0264140 A1 | 10/2011 | Lizardi et al. | |
| 2013/0035721 A1 * | 2/2013 | Brunelle | A61B 17/0401 606/232 |
| 2013/0085528 A1 | 4/2013 | DiMatteo et al. | |
| 2013/0103080 A1 | 4/2013 | Hernandez | |
| 2013/0158597 A1 * | 6/2013 | Hernandez | A61B 17/0401 606/232 |
| 2013/0158599 A1 | 6/2013 | Hester et al. | |
| 2013/0267998 A1 | 10/2013 | Vijay et al. | |
| 2013/0338710 A1 | 12/2013 | Heaven et al. | |
| 2014/0257355 A1 * | 9/2014 | Palese | A61B 17/0401 606/232 |
| 2014/0257381 A1 * | 9/2014 | Palese | A61B 17/0401 606/232 |
| 2014/0277150 A1 | 9/2014 | Jones et al. | |
| 2014/0316461 A1 | 10/2014 | Sklar | |
| 2014/0364906 A1 | 12/2014 | Palese et al. | |
| 2015/0018878 A1 | 1/2015 | Rizk et al. | |
| 2016/0128682 A1 | 5/2016 | Konrath et al. | |
| 2016/0310125 A1 | 10/2016 | Spivey et al. | |
| 2022/0039791 A1 | 2/2022 | Miller et al. | |

FOREIGN PATENT DOCUMENTS

| | | |
|---|---|---|
| JP | 4945574 B2 | 6/2012 |
| WO | WO-2007078978 A2 | 7/2007 |
| WO | WO-2009076526 A1 | 6/2009 |
| WO | WO-2013169905 A1 | 11/2013 |
| WO | WO-2014033692 A2 | 3/2014 |
| WO | WO-2015127057 A1 | 8/2015 |
| WO | WO-2017003442 A1 | 1/2017 |

OTHER PUBLICATIONS

U.S. Appl. No. 15/458,007, filed Mar. 13, 2017, Adam Gustafson et al.

U.S. Appl. No. 16/281,549, filed Feb. 21, 2019, Adam Gustafson et al.

U.S. Appl. No. 16/459,984, filed Jul. 2, 2019, Gerome Miller et al.

U.S. Appl. No. 17/479,483, filed Sep. 20, 2021, Gerome Miller et al.

Zhao et al., "Treatment of calcaneal avulsion fractures with TwinFix suture anchors fixation," China Journal of Orthopaedics and Traumatology, No. 6, Jun. 25, 2011.

Extended European Search Report for EP App. No. 18161239.1 mailed Aug. 14, 2018 (7 pages).

Extended European Search Report for EP App. No. 18161276.3 mailed Aug. 10, 2018 (7 pages).

\* cited by examiner

METHODS AND SYSTEMS FOR KNOTLESS SUTURE ANCHORING

CROSS REFERENCE TO RELATED APPLICATIONS

The present application is a continuation U.S. patent application Ser. No. 16/281,549 (now U.S. Pat. No. 11,123,060) entitled "Methods and Systems for Knotless Suture Anchoring" filed Feb. 21, 2019, which is a divisional of U.S. patent application Ser. No. 15/458,007 (now U.S. Pat. No. 10,245,020) entitled "Methods and Systems for Knotless Suture Anchoring" filed Mar. 13, 2017, which are hereby incorporated by reference in their entireties.

BACKGROUND

Tearing of, or the complete or partial detachment of ligaments, tendons and/or other soft tissues from their associated bones within the body are commonplace injuries, particularly among athletes. Such injuries generally result from excessive stresses being placed on these tissues. By way of example, tissue tearing or detachment may occur as the result of an accident such as a fall, over-exertion during a work-related activity, or during the course of an athletic event. In the case of tearing or a partial or complete detachment of soft tissue from a bone, surgery is typically required to reattach the soft tissue (or a graft tissue) to the bone.

Numerous devices have been used to secure soft tissue to bone. Examples of such devices include screws, tacks, staples, suture anchors, and suture alone. In soft tissue repair or re-attachment procedures utilizing suture anchors, an anchor-receiving hole is drilled into bone at the desired point of fixation or tissue re-attachment, and a suture anchor is deployed into the hole using an appropriate installation tool. A suture, coupled to the anchor and passed through or around the soft tissue, thus becomes effectively locked to the bone, which secures the soft tissue to the bone.

During a suture anchoring procedure, it can be challenging to deploy the suture anchor into the anchor-receiving hole. Further, existing suture anchors and inserter devices used to insert the anchors into bone may have certain disadvantages that complicate their use and/or impose certain undesirable limits. Also, procedures that require the suture to be tied into a knot can be time-consuming and cumbersome due to inherent space constraints, which can complicate a surgery.

Accordingly, there is a need for improved methods and systems for attaching tissue to bone.

SUMMARY

In at least some aspects, a surgical system is provided that in some embodiments includes an outer shaft having a lumen extending therethrough, a suture anchor including a first anchor body and a second anchor body, and an elongate inner shaft. The first anchor body has a distal portion, a proximal portion, and a first lumen extending longitudinally therethrough. The second anchor body has a distal end mated to a proximal end of the first anchor body and has a second lumen extending therethrough that is configured to receive the proximal portion of the first anchor, the second anchor body having at least one opening extending through a side wall of the second anchor body at a position offset from proximal and distal ends thereof. The elongate inner shaft is configured to be removably received within the lumen of the outer shaft and through the first and second anchor bodies such that a distal end of the inner shaft protrudes beyond a distal end of the distal portion, the inner shaft having a driver shaft portion configured to be removably coupled to the first anchor body within the first lumen such that the inner shaft is configured to be rotated to cause the proximal portion of the first anchor body to move proximally into the second lumen and to occlude the opening of the second anchor body.

The surgical system can vary in many different ways. For example, the opening can be in the form of first and second openings formed through opposed side walls of the proximal anchor body. As another example, the outer shaft can have a mating feature extending from a distal end thereof and configured to releasably mate with a corresponding mating feature formed at the proximal end of the second anchor body. As another example, the proximal portion of the first anchor body can have a thread formed thereon. As a further example, a proximal end of the second anchor body can be configured to be releasably coupled to the outer shaft.

In at least some embodiments, the inner shaft has a proximal handle coupled thereto. Further, in at least some embodiments, the first lumen of the first anchor body has a locking component configured to releasably mate with the driver shaft portion of the inner shaft.

In at least some aspects, a suture anchor is provided that in some embodiments includes a distal anchor body and a proximal anchor body. The distal anchor body has a distal portion, a proximal portion, and an outer wall defining a first lumen that extends through the distal anchor body. The proximal anchor body has a distal end mated to a proximal end of the distal anchor body, the proximal anchor body having an outer wall defining a second lumen that extends through the proximal anchor body and at least one opening formed through a side wall of the outer wall that are offset from the distal end and a proximal end of the proximal anchor body. The second lumen is configured to receive the proximal portion of the distal anchor body therein when a locking force is applied to the distal anchor body.

The suture anchor can vary in many different ways. For example, the opening can be in the form of first and second openings formed through opposed side walls of the outer wall of the proximal anchor body. As another example, the distal portion of the distal anchor body can be distally tapered. In at least some embodiments, the distal portion of the distal anchor body has a proximal shoulder having the proximal portion of the distal anchor body extending therefrom, an outer diameter of the shoulder being greater than an outer diameter of the proximal portion. The proximal shoulder can abut the distal end of the proximal anchor body when the proximal portion of the distal anchor body is received within the proximal anchor body.

In at least some embodiments, the proximal portion of the distal anchor body has an external thread formed thereon that is configured to mate with a corresponding thread formed in the second lumen of the proximal anchor body.

In at least some embodiments, the locking force is a rotational force that causes the distal anchor body to be threaded proximally into the proximal anchor body.

In at least some embodiments, the proximal anchor body has at least one bone engaging feature formed thereon.

In at least some aspects, a method of performing a surgical repair is provided that in some embodiments includes driving an anchor assembly comprising a proximal anchor body mated to a proximal end of a distal anchor body of the anchor assembly into a hole in a bone, the proximal anchor body having at least one suture passed through at least one opening formed through at least one side of the proximal anchor body, the suture being passed through the opening such that terminal end portions of the suture pass alongside a driver shaft removably attached to the anchor assembly, the suture having a portion thereof that is attached to soft tissue. The method also includes rotating the distal anchor body to cause the distal anchor body to move proximally towards the proximal anchor body such that a proximal portion of the distal anchor body is received within the proximal anchor body so as to occlude the opening and thereby cause the suture to be secured between an inner wall of the proximal anchor body and an outer wall of the distal anchor body.

The method can vary in many different ways. For example, the opening can include first and second openings formed through opposed sides of the proximal anchor body. As another example, the method can further include forming the hole in the bone using a distal end of the driver shaft, the driver shaft extending through the anchor assembly. As another example, the method can further include tensioning the suture while driving the anchor assembly into the bone. As a further example, the method can further include tensioning the suture while rotating the distal anchor body. In at least some embodiments, rotating the distal anchor body to cause it to move proximally towards the proximal anchor body includes rotating the driver shaft.

BRIEF DESCRIPTION OF THE DRAWINGS

The present disclosure will be more fully understood from the following detailed description taken in conjunction with the accompanying drawings, in which.

DETAILED DESCRIPTION

Figure 1A:
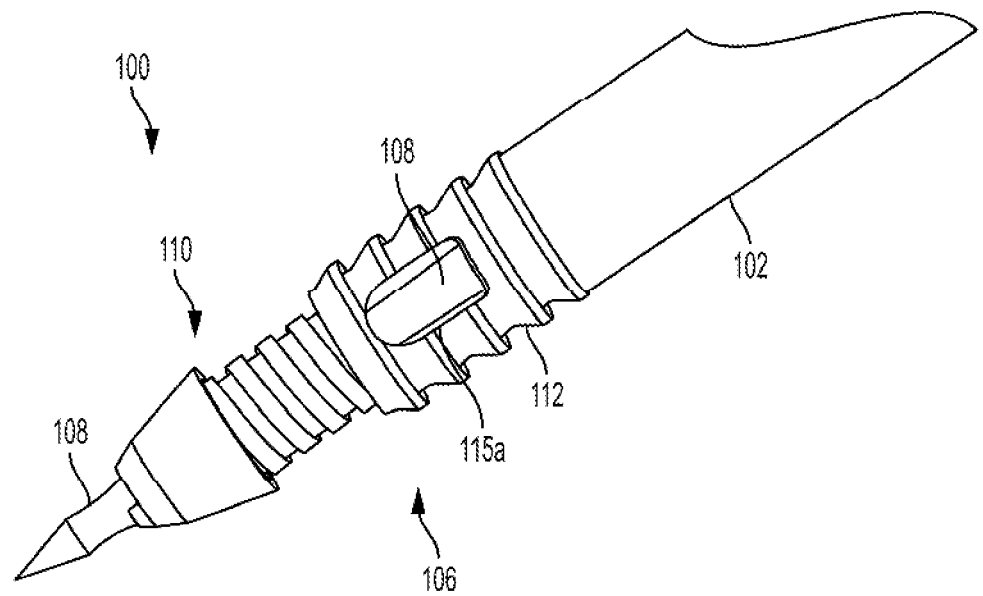
FIG. 1A is a perspective view of one embodiment of a surgical system.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the systems, devices, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various methods, systems, and devices are provided for securing tissue to bone. In general, the methods, systems, and devices can facilitate securing suture to tissue. In some embodiments, a surgical system for attaching tissue to bone includes an outer shaft having a lumen extending therethrough, an inner shaft configured to be removably received within the lumen of the outer shaft, and an implantable suture anchor assembly. The suture anchor assembly includes a distal first anchor body and a proximal second anchor body configured such that at least a portion of the distal first anchor body can move proximally into the proximal second anchor body. For example, in some embodiments, a proximal portion of the first anchor body can be received within a lumen extending longitudinally through the second anchor body.

The second anchor body has one or more openings extending through a side wall or through opposed side walls of the second anchor body at positions offset from proximal and distal ends thereof. In an assembled configuration, the second anchor body has a distal end thereof mated to a proximal end of the first anchor body. The second anchor body can be removably mated to a distal end of the outer shaft. In the assembled configuration, the inner shaft extends through the outer shaft and the first and second anchor bodies (pre-coupled to one another) so as to protrude from a distal end of the distal first anchor body. The inner shaft, which is also referred to herein as a driver shaft, has a driver shaft portion configured to be removably coupled to the first anchor body within a lumen extending longitudinally through the first anchor body. In this way, the inner shaft is configured to be rotated to cause a proximal portion of the first anchor body to move proximally into the lumen in the second anchor body and to occlude the openings in the second anchor body.

A method for performing a surgical repair to attach or reattach soft tissue to bone is also provided. In some embodiments, the method includes initiating a hole in bone by inserting a distal end of the inner shaft into a bone, the inner shaft extending through the outer shaft and through the suture anchor assembly such that the distal first anchor body is releasably coupled to a portion of the inner shaft. The method also includes passing at least one suture through at least one opening formed in a side wall (or in opposed side walls) of the proximal second anchor body such that terminal end portions of the suture pass alongside a driver shaft removably attached to the suture anchor assembly. The suture, which can be in the form of multiple sutures, has a portion thereof that is attached to soft tissue that is to be reattached to the bone. In some embodiments, the suture can be coupled to the suture anchor assembly before the suture anchor assembly is delivered to a desired location in bone and the inner shaft coupled to the suture anchor assembly is used to initiate a bone hole. The method further includes driving the suture anchor assembly into the hole formed in the bone. In particular, a suitable force-applying instrument can be used to drive the inner shaft with the suture anchor assembly loaded thereto deeper in the bone hole, to complete the formation of the bone hole. The suture can be tensioned while the suture anchor assembly is being driven into the bone hole.

Once the suture anchor assembly is delivered to a desired depth in the bone hole, the method includes applying locking force to the distal first anchor body to cause it to move proximally towards the proximal second anchor body such that the proximal portion of the first anchor body is received within the second anchor body. The locking force can be rotational force, and the distal first anchor body can be rotated by rotating the inner shaft, a portion of which is coupled to the first anchor body. The suture can be tensioned while the first anchor body is being rotated. The proximal portion of the first anchor body is received within the second anchor body so as to occlude the openings to cause the suture to be secured between an inner wall of the proximal anchor body and an outer wall of the distal anchor body. The suture can also be secured between the bone and the side wall of the proximal anchor body.

FIGS. 1A-7C illustrate one embodiment of a surgical system 100 that includes an outer shaft 102 having a lumen 104 extending therethrough, an implantable anchor assembly including a suture anchor 106, and an elongate awl shaft or inner shaft 108 configured to be removably received within the lumen 104 of the outer shaft 102. The anchor assembly includes the suture anchor 106 that includes a cannulated first anchor body 110, which is referred to herein as a distal anchor body, and a cannulated second anchor body 112, which is referred to herein as a proximal anchor body, configured such that at least a portion of the first anchor body 110 can be inserted proximally into the second anchor body 112, as discussed in more detail below. The second anchor body 112 is disposed proximally to the first anchor body 110, and it has first and second openings 115a, 115b extending through opposed side walls thereof. It should be appreciated that, in some embodiments, the second anchor body 112 can have a single opening extending through a side thereof.

Figure 2:
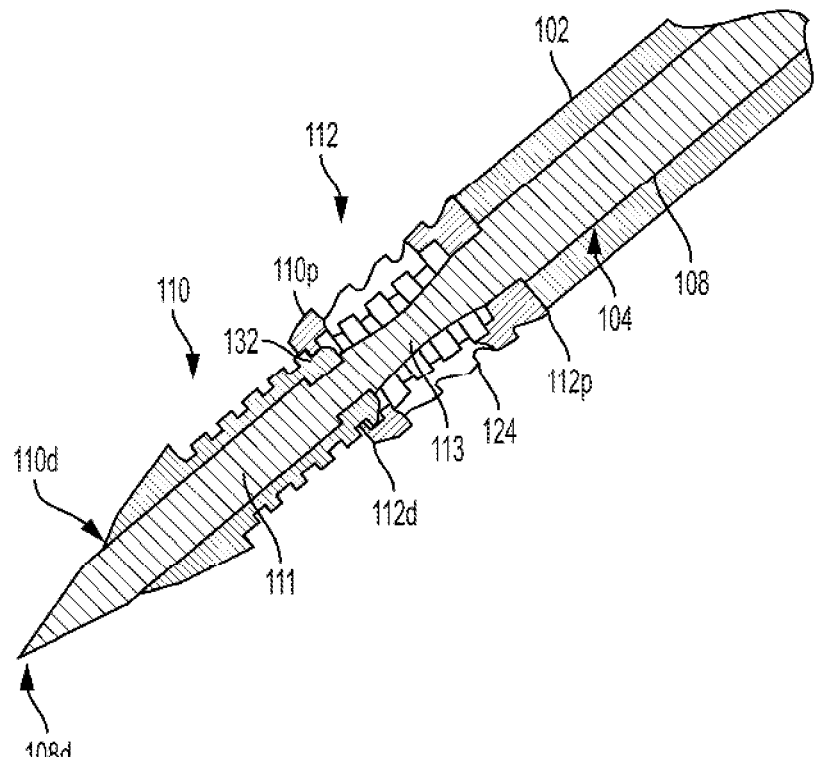
FIG. 2 is a cross-sectional view of the surgical system of FIG. 1A.

The first anchor body 110 has proximal and distal ends 110p, 110d and a lumen 111 extending longitudinally therethrough. The second anchor body 112 has proximal and distal ends 112p, 112d and a lumen 113 extending longitudinally therethrough. The first anchor body 110 can be pre-coupled to the second anchor body 112 before the first anchor body 110 is driven into the lumen 113 in the second anchor body 112. When pre-coupled as shown in FIGS. 1A and 2, the distal end 112d of the second anchor body 112 contacts the proximal end 110p of the first anchor body 110.

Figure 6A:
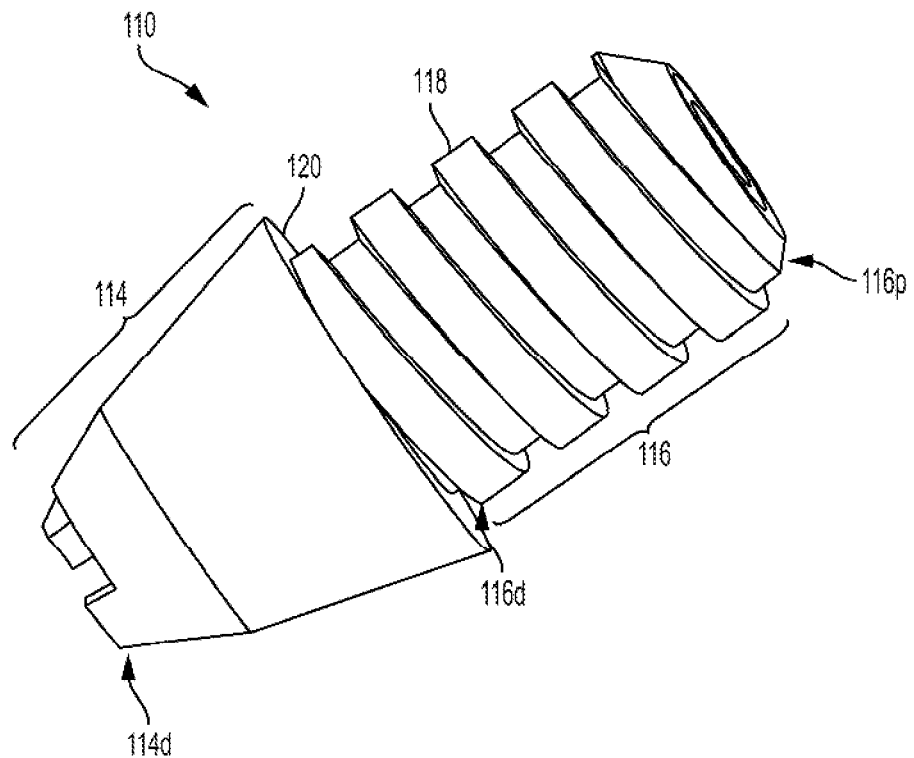
FIG. 6A is a perspective view of a first anchor body of the surgical system of FIG. 1A.

The first anchor body 110 can have various configurations. In the illustrated embodiment, as shown in FIGS. 1A, 1B, and 6A-6C, the first anchor body 110 having the lumen 111 extending therethrough has a distal portion 114 and a proximal portion 116 extending from the distal portion 114. The distal portion 114 is configured to form a bone hole initiated by the distal tip of the inner shaft 108. In this example, the distal portion 114 is generally shaped as a truncated cone, and it can have distal features extending from its distal end. In some embodiments, however, the distal portion 114 can have one or more flat faces, or it can be configured it any other way. As shown in FIG. 6A, the distal portion 114 is distally tapered and has a proximal shoulder 120 having the proximal portion 116 extending therefrom. As shown, the distal portion 114 can have a distal-most portion 114d terminating at the distal end 110d of the first anchor body that is more tapered than a more proximal portion of the distal portion 114. The distal portion 114 is configured as a dilator feature that can widen a hole in bone once the hole is initiated, such as with a distal end of the elongate shaft 108.

In the example illustrated, an outer diameter of the proximal shoulder 120 is greater than an outer diameter of the proximal portion 116, and the proximal portion 116 is formed such that its outer wall at a distal end 116d thereof is offset from an outer edge of the proximal shoulder 120. It should be appreciated, however, that the first anchor body 110 can have other suitable configurations. For example, the first anchor body 110 may not have a shoulder similar to the proximal shoulder 120. Also, a diameter of the proximal-most portion of the distal portion of the first anchor body can be the same as that of the proximal portion of the first anchor body.

The proximal portion 116 has an external thread 118 formed on an outer wall thereof. In this way, the proximal portion 116 of the first anchor body 110 can be in the form of a male threaded boss configured to be received by a complimentary-shaped female feature formed in the second anchor body 112. In particular, as in the illustrated embodiment, the external thread 118 formed on the proximal portion 116 of the first anchor body 110 is configured to mate with a corresponding thread formed in the lumen 113 of the second anchor body 112. Thus, as shown in FIGS. 2 and 7A-7C, the lumen 113 in the second anchor body 112 has a thread 122 formed therein such that the proximal portion 116 of the first anchor body 110 can be threaded proximally into the lumen 113 in the second anchor body 112.

The second anchor body 112 can also have various configurations. In the illustrated embodiment, as shown in FIGS. 1A, 1B, and 7A-7C, the second anchor body 112 having the lumen 113 extending therethrough is generally cylindrical and has one or more bone engaging features, e.g., ribs 124, formed on its outer wall. However, the second anchor body 112 can have other bone engaging features formed thereon, such as threads.

Figure 7A:
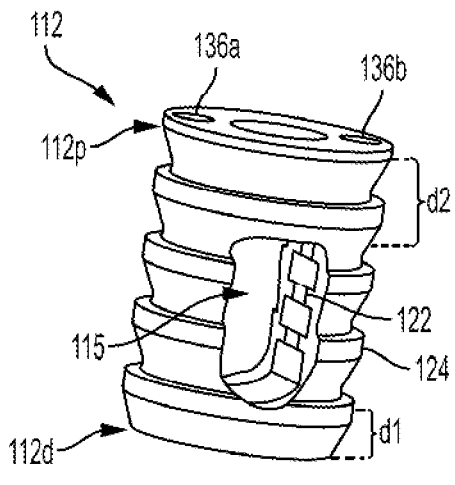
FIG. 7A is a perspective view of a second anchor body of the surgical system of FIG. 1A.
Figure 7B:
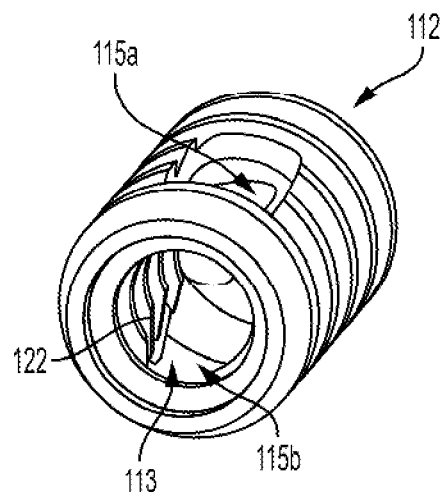
FIG. 7B is another perspective view of the second anchor body of FIG. 7A.

In the illustrated embodiment, the second anchor body 112 has the first and second openings 115a, 115b extending through opposed side walls thereof at positions offset from the proximal and distal ends 112p, 112d thereof. As shown in FIG. 7A, the openings 115a, 115b are formed through the side walls of the second anchor body 112 such that they define, together with the lumen 113, a tunnel or passageway 115 extending laterally across the second anchor body 112. As shown in FIG. 7A, each of the openings 115a, 115b is formed such that its distal end is offset from the distal end 112d of the second anchor body 112 at a first distance d1 that is smaller than a second distance d2 between the proximal end 112p of the second anchor body 112 and a proximal end of each of the openings 115a, 115b. It should be appreciated, however, that the openings 115a, 115b can be offset at any suitable distances (e.g., substantially the same) from the opposed ends of the second anchor body, including at different distances among the openings. Also, although two openings are shown, one or more than two openings can be formed in some embodiments. For example, in at least one embodiment, one opening can be is formed through a side wall of the second anchor body 112. The single opening can be formed similar to one of the first and second openings 115a, 115b.

Figure 1B:
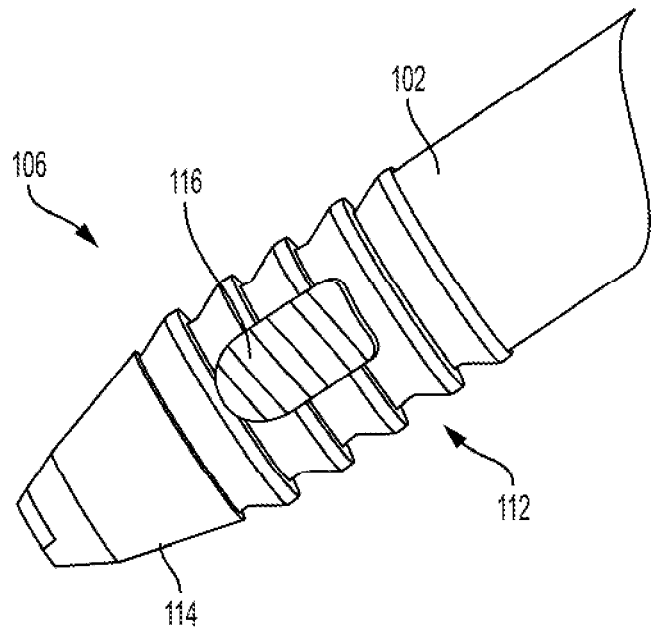
FIG. 1B is a perspective view of a suture anchor assembly of the surgical system of FIG. 1A.

The openings 115a, 115b can be used to pass at least one suture through the second anchor body 112, as discussed in more detail below. Further, in use, when the proximal portion 116 of the first anchor body 110 is inserted into the lumen 113 of the second anchor body 112, the openings 115a, 115b are blocked or occluded, as shown in FIG. 1B. This causes the suture to be pinched between the inner wall of the second anchor body 112 and the outer wall of the first anchor body 110.

In an assembled configuration of the surgical system 100, before the system 100 is inserted into bone, as shown in FIGS. 1A, 1B, 2, and 4, the elongate inner shaft 108 is received within the lumen 104 of the outer shaft 102 and through the first and second anchor bodies 110, 112 such that a distal end 108d of the inner shaft protrudes beyond the distal end 110d of the first anchor body 110. The inner shaft 108 is configured to initiate a hole in a bone, and the hole can be dilated with the distal portion 114 of the first anchor body 110, as discussed in more detail below.

In some embodiments, the inner shaft 108 and the lumen 111 of the first anchor body 110 can be configured such that the shaft 108 can be releasably locked within the lumen 111. For example, a distal portion of the inner shaft 108 can fit within a key-hole type feature formed in the lumen 111 that can be configured to releasably lock the distal portion of the inner shaft 108 therewithin. Any suitable lock/key-type configuration of the lumen 111 and the inner shaft 108 can be implemented.

Figure 3:
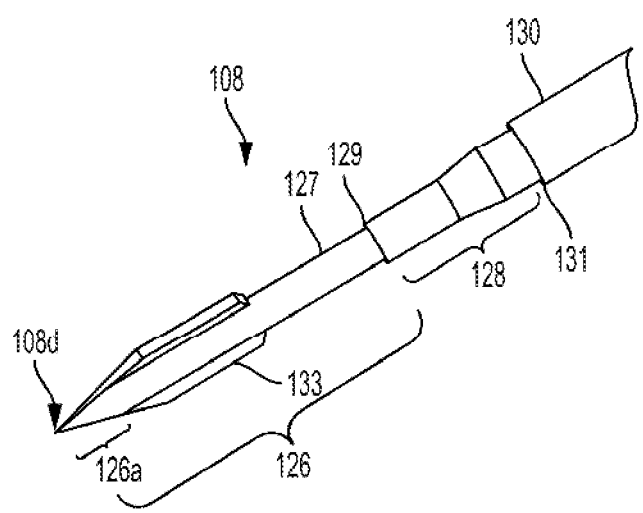
FIG. 3 is a perspective view of an inner shaft of the surgical system of FIG. 1A.
Figure 4:
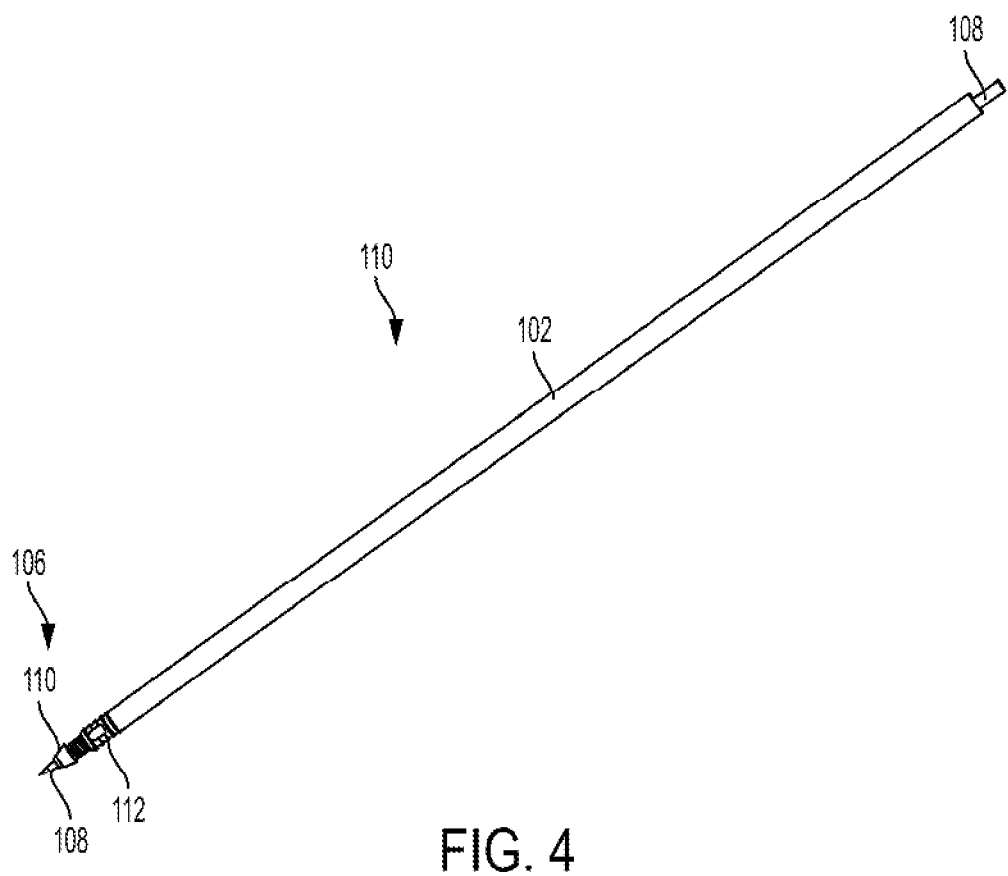
FIG. 4 is another perspective view of the surgical system of FIG. 1A.

In the illustrated embodiment, as shown in shown in FIG. 3, the inner shaft 108 has a distal driver shaft portion 126, an intermediate portion 128, and a proximal portion 130. The intermediate portion 128 can extend through the second anchor body 112. The driver shaft portion 126 terminates at the distally tapered distal end 108d and is configured to be removably coupled to the first anchor body 110. The driver shaft portion 126 can have mating features configured to mate with corresponding mating features of the lumen 111 of the first anchor body 110. For example, the driver shaft portion 126 can have protrusions or blade features 133 (two, in this example, though any number can be formed) extending proximally from a distally tapered end portion (shown as a portion 126a in FIG. 3) terminating at the distal end 108d. A more proximal part 127 of the distal portion 126 having, in this example, a smaller outer diameter than the blade features 133, can be configured to engage the proximal end 110p of the first anchor body 110.

Figure 6B:
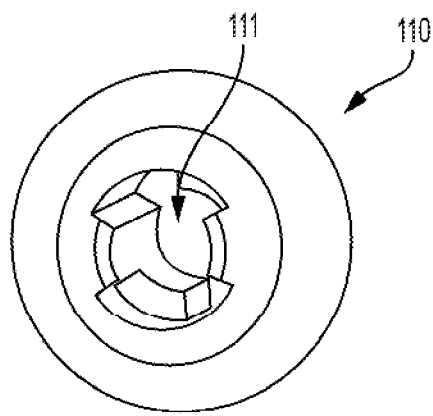
FIG. 6B is another perspective view of the first anchor body of FIG. 6A.
Figure 6C:
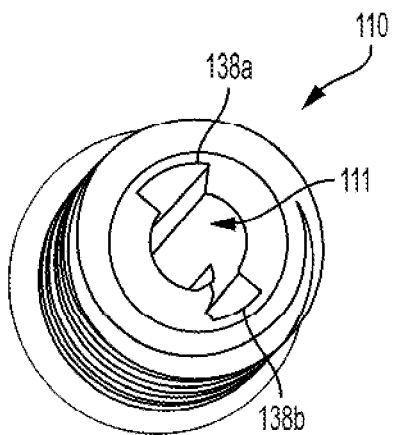
FIG. 6C is another perspective view of the first anchor body of FIG. 6A.

The blade features 133 can be configured to engage the lumen 111 in the first anchor body 110. For example, the lumen 111 can have a locking component configured to reversibly engage the blade features 133 of the inner shaft 108. FIGS. 6B and 6C illustrate that the lumen 111 has key-hole features 138a, 138b formed on opposed sides from a central part of the lumen 111. The lumen 111 in the first anchor body 110 can be configured such that its more distal part is larger than the more proximal portion of the lumen 111 adjacent to the proximal end 110p. This more distal part of the lumen 111 can be configured as a locking component that can lockingly receive therein the distal portion 126 of the inner shaft 108. For example, when the inner shaft 108 in inserted into the lumen 111 (e.g., pushed distally while a force is applied), the blade features 333 enter the lumen 111 through the key-hole features 138a, 138b, which extend distally into the lumen 111 towards the inner locking component configured to engage the blade features 133. The blade features 133 engage the locking component and, once the inner shaft 108 is rotated, the inner shaft 108 becomes locked within the lumen 111. In the locked position, the inner shaft 108 prevents the first anchor body 110 from axial movement, and in this position the inner shaft 108 can be rotated to cause the first anchor body 110 coupled thereto to be also rotated. To unlock the inner shaft 108, the inner shaft 108 can be rotated (e.g., by 90 degrees) and it can be removed from the first anchor body 110.

Thus, the inner shaft 108 can be inserted into the lumen 111 and the inner shaft 108 can be rotated to be locked within the lumen 111, to thus prevent axial movement of the first anchor body 110 with respect to the inner shaft 108. In such a position of the inner shaft 108, the inner shaft 108 can be used to drive the suture anchor 106 into the bone and to be rotated to cause the first anchor body 110 to be driven into the second anchor body 112. The inner shaft 108 in the first, locked position can be rotated (e.g., by 90 degrees) so as to be disengaged from the distal part of the lumen 111 such that the inner shaft 108 can be separated from the first anchor body 110.

The first anchor body 110 can be coupled to the driver shaft portion 126 of the inner shaft 108 in various ways. For example, the driver shaft portion 126 can be held within the lumen 111 via a friction fit or using another engagement approach. As shown in FIG. 2, the proximal end 110p of the first anchor body 110 can have one or more mating features, such as, e.g., a circular protrusion 132 configured to engage feature at a proximal end of the driver shaft portion 126. Additionally or alternatively, the first anchor body 110 can have female feature(s) configured to mate with complementary male feature(s) formed on a portion (e.g., the driver shaft portion 126) of the inner shaft 108.

As shown in FIGS. 1A and 1B, the first anchor body 110, coupled to the inner shaft 108, is pre-coupled to the second anchor body 112. In this way, when a locking force, such as a rotational force, is applied to the inner shaft 108, the first anchor body 110 coupled to the inner shaft 108 is caused to be threaded into the lumen 113 in the second anchor body 112. It should be appreciated, however, that the first anchor body 110 can be releasably coupled to the inner shaft 108 (e.g., to the driver shaft portion 126) in any suitable way.

As also shown in FIG. 2, the intermediate portion 128 of the inner shaft 108 extends through the lumen 113 in the second anchor body 112 without engaging the lumen 113, such that the inner shaft 108 can move within the second anchor body 112. The intermediate portion 128 extends between the distal portion 126 and the proximal portion 130 such that the intermediate portion 128 terminates at a distal shoulder 131 of the proximal portion 130. In the assembled configuration of the system 100, as shown in FIG. 1A, the intermediate portion 128 of the inner shaft 108 can be visible through the openings 115a, 115b formed through the second anchor body 112.

Figure 5:
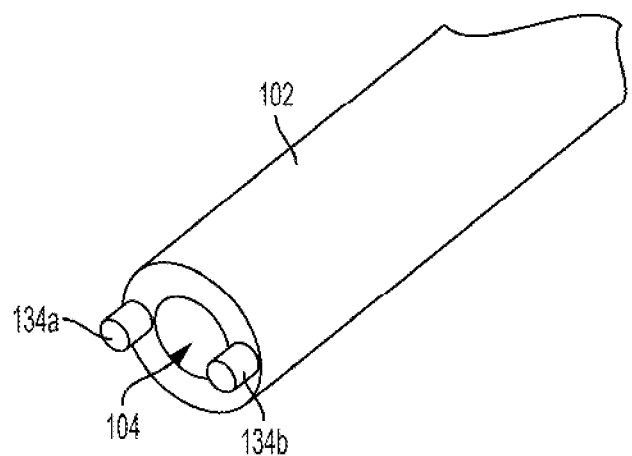
FIG. 5 is a perspective view of a distal portion of an outer shaft of the surgical system of FIG. 1A.
Figure 7C:
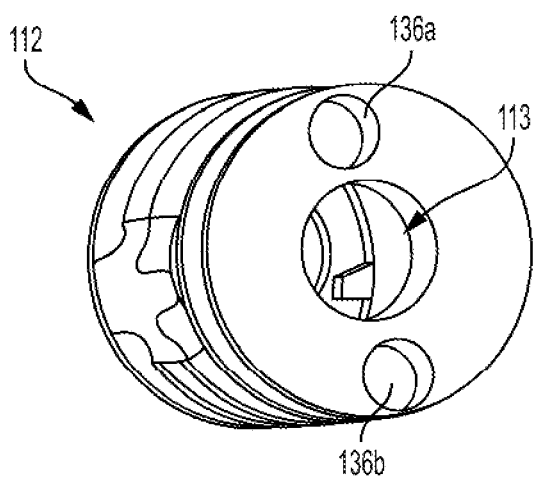
FIG. 7C is another proximal view of the second anchor body of FIG. 7A.

In the assembled configuration of the system 100, as shown in FIG. 2, the second anchor body 112 is disposed such that its proximal end 112p abuts the shoulder 131. As shown in FIG. 2, the outer shaft 102 having the inner shaft 108 extending therethrough is disposed such that the proximal end 112p of the second anchor body 112 abuts a distal end 102d of the outer shaft 102. In some embodiments, the outer shaft 102 has a mating feature extending from the distal end 102d thereof that is configured to releasably mate with a corresponding (e.g., complementary) mating feature formed at the proximal end 112p of the second anchor body 112. For example, as shown in FIG. 5, the distal end 102d of the outer shaft 102 can have protrusions 134a, 134b formed on opposed sides of the lumen 104. The protrusions 134a, 134b can be configured to releasably mate complementary recesses or openings 136a, 136b formed at the proximal end 112p of the second anchor body 112, as shown in FIGS. 7A and 7C. It should be appreciated, however, that the outer shaft 102 can have one or more mating features of any suitable configuration that are configured to releasably mate with corresponding mating feature(s) formed at the second anchor body 112.

FIGS. 8A-8E illustrate one embodiment a method of performing a surgical repair. The method is described, by way of example, as performed using the system 100 shown in FIGS. 1A-7C, though it should be appreciated that the surgical repair method can be performed using other surgical systems, including surgical systems in which one or more components are different from those included in the surgical system 100.

Figure 8A:
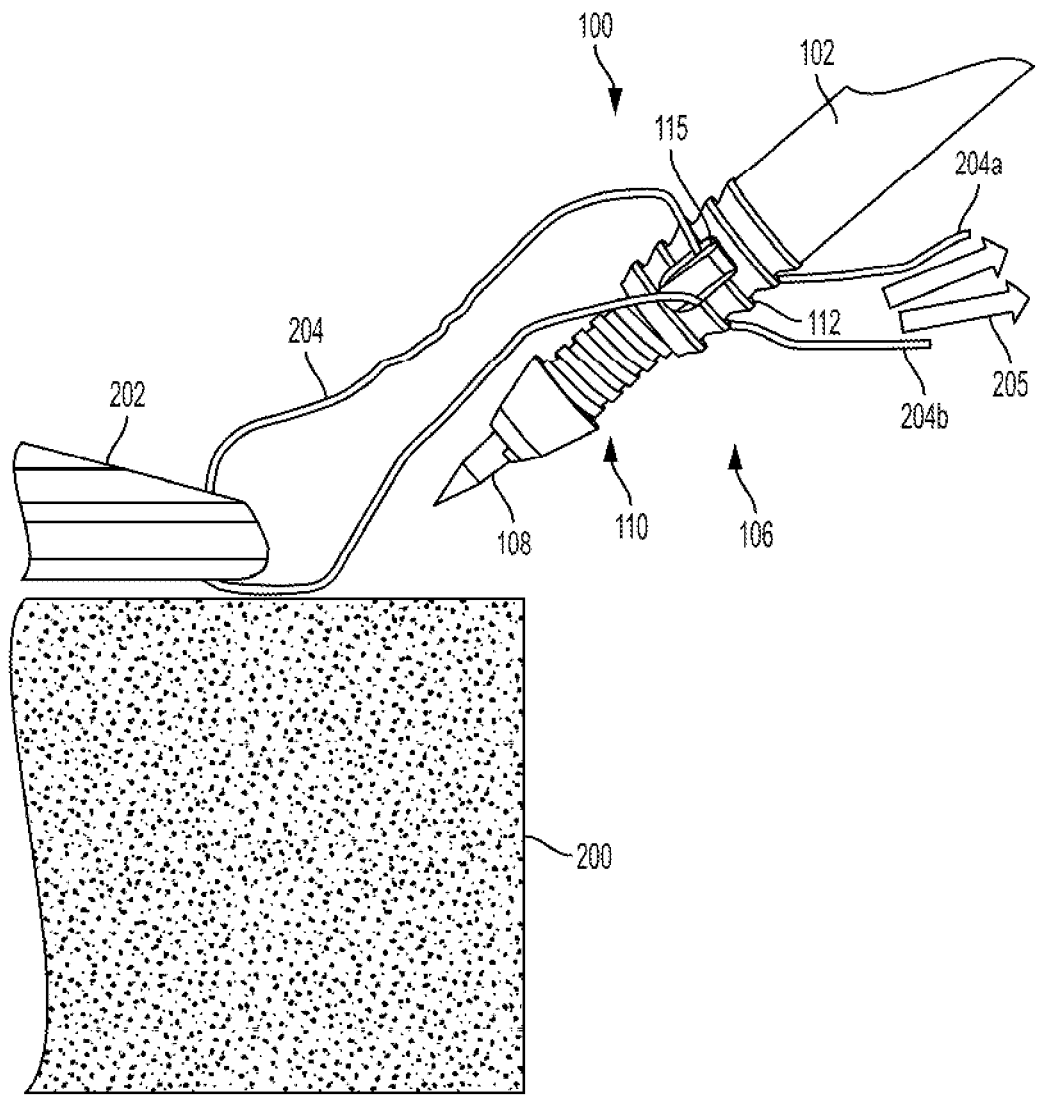
FIG. 8A illustrates the surgical system of FIG. 1A, showing a suture coupled to the system, and the system delivered to a bone.

FIG. 8A illustrates bone 200 and soft tissue 202 (e.g., a tendon) that is to be attached to the bone 200 using the surgical system 100, which is shown in the assembled configuration. In particular, as shown, the inner shaft 108 extends through the outer shaft 102 and through an implantable anchor assembly including the first anchor body 110 (to which the inner shaft 108 is coupled) and the second anchor body 112 such that the inner shaft's distal end 108d protrudes from the first anchor body 110. The proximal end of the first anchor body 110 is mated to the distal end of the second anchor body 112 that is coupled to the distal end of the outer shaft 102.

Figure 8C:
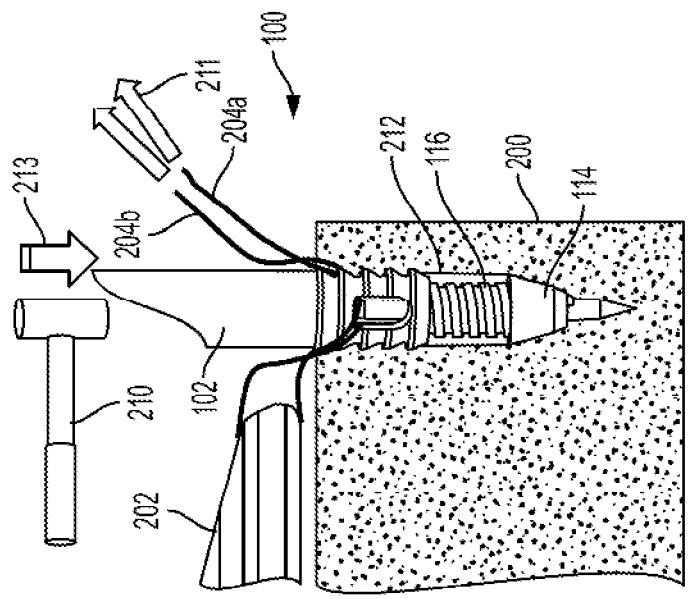
FIG. 8C illustrates the surgical system of FIG. 8B, showing a distal end of an inner shaft driven distally into the bone.
Figure 8B:
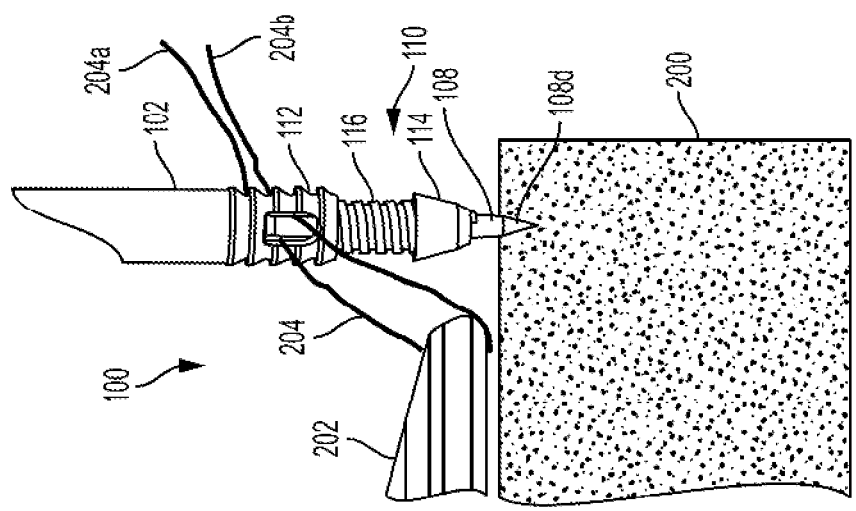
FIG. 8B illustrates the surgical system of FIG. 8A, showing a distal end of an inner shaft initiating a hole in the bone.

As shown in FIGS. 8A and 8B, a suture 204 is coupled to the tissue 202, such as by being passed through and/or wrapped around tissue 202. As shown in FIG. 8A, terminal end portions 204a, 204b of the suture 204 are passed through the second anchor body 112, as schematically shown by arrows 205, such that the terminal end portions 206a, 206b extend through the openings 115a, 115b extending through the opposed sides of the second anchor body 112 and communicating with the lumen 113 in the second anchor body 112. In particular, the suture 204 is passed across the second anchor body 112 by being passed through one of the openings 115a, 115b in the second anchor body 112, across the lumen 113, and through another one of the openings 115a, 115b. The terminal end portions 204a, 204b enter the lumen 113 from one side of the second anchor body 112 and exit the lumen 113 from the opposed side of the second anchor body 112, and the terminal end portions 204a, 204b extend at opposed sides of the inner shaft 108. It should be appreciated that the single suture 204 is shown by way of example only, as multiple sutures can be used to couple the tissue 202 to the bone 200. The terminal end portions 206a, 206b can be passed alongside a portion of the inner shaft 108. The relatively large size of the openings 115a, 115b enables the use of multiple sutures to attach soft tissue to bone.

Additionally, in some embodiments, the terminal end portions 204a, 204b of the suture 204 can be passed through only one of the first and second openings 115a, 115b. The terminal end portions 204a, 204b pass through that one opening and extend through the lumen 104 of the outer shaft 102. The terminal end portions 204a, 204b can thus extend from a proximal end of the lumen 104.

Furthermore, in other embodiments as mentioned above, a single opening can be formed through a side wall of the second anchor body 112. In such embodiments, the terminal end portions 204a, 204b pass through the single opening and extend through the lumen 104 of the outer shaft 102. For example, the terminal end portions 204a, 204b can extend from a proximal end of the lumen 104.

Also, although two openings are shown, one or more than two openings can be formed in some embodiments. For example, in at least one embodiment, one opening can be is formed through a side wall of the second anchor body 112. The single opening can be formed similar to one of the first and second openings 115a, 115b.

FIG. 8B shows the system 100 loaded with the suture 204 delivered to a desired location in the bone 200 and shows the tip or distal end 108d of the inner shaft 108 is used to initiate a hole in the bone 200. As shown, the distal end 108d is driven into the bone 200 at an initial depth at the desired location. This initiates a hole in the bone 200. While tension is maintained on the terminal end portions 204a, 204b of the suture 204 (as shown schematically by arrows 211), the inner shaft 108 with the anchor assembly is driven into the bone 200, as shown in FIG. 8C. FIG. 8C shows that a suitable instrument 210, such as mallet, hammer, or other instrument, is used to insert the self-punching shaft 108 into the bone 200. The instrument 210 can be used to impact (as shown schematically by an arrow 213) the proximal end of the inner shaft 108 to drive the inner shaft 108 into bone 200. In this way, a portion of the inner shaft 108 extending through the first and second anchor bodies 110, 112 is inserted deeper into the desired location in bone 200. The distal portion 114 of the first anchor body 110 dilates the hole initiated by the inner shaft's distal end 108d. As the inner shaft 108 is driven distally, the bone hole 212 is formed and the first and second anchor bodies 110, 112 are positioned with the hole 212 such that they sit distal to or below the surface of the bone 200, as shown in FIG. 8C. In some embodiments, however, a portion of the second anchor body 112 can sit above the surface of the bone 200. The inner shaft 108 can be inserted into the bone 200 at a depth that is sufficient to hold the suture anchor 106 at a desired position relative to the bone 200.

As shown in FIG. 8C, the tissue 202 coupled to the suture 204 is positioned at a desired location adjacent to the bone hole 212. When tension is maintained on the terminal end portions 204a, 204b of the suture 204, the tissue 202 can be brought closer to the bone hole 212 to position it relative to the bone 200 as desired.

Once the inner shaft 108 with the suture anchor assembly is inserted into the bone 200 so as to form the bone hole 212 in the desired location, the first anchor body 110 is rotated to cause it to move proximally towards the proximal second anchor body 112 such that the proximal portion 116 of the first anchor body 110 is received within the second anchor body 112 so as to occlude the openings 115a, 115b. This causes the suture 104 to be secured between the bone and the side wall of the second anchor body 112 and between inner walls of the second anchor body 112 component and an outer wall of the first anchor body 110.

Figure 8D:
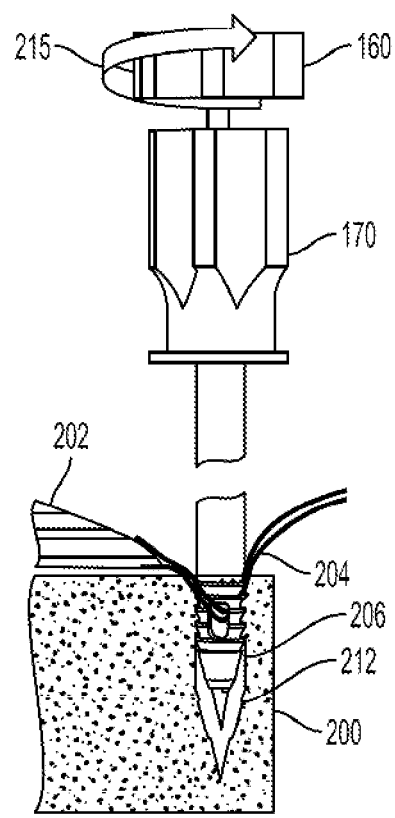
FIG. 8D illustrates the surgical system of FIG. 8C, showing the inner shaft rotated.

Locking force can be applied to the first anchor body 110 to cause its proximal portion 116 to engage with the second anchor body 112. FIG. 8D illustrates that a proximal handle 160 coupled proximally to the inner shaft 108 can be rotated (as shown schematically by an arrows 215), to cause the shaft 108 to rotate and to thereby cause the proximal portion 116 of the first anchor body 110 to move proximally into the lumen 113 in the second anchor body 112. As a result, the proximal shoulder 120 of the first anchor body 110 abuts the distal end 112d of the second anchor body 112. The outer shaft 102 can be used to apply force to the suture anchor assembly 106 while the inner shaft 108 is rotated. FIG. 8D also shows that the outer shaft 102 can have a proximal handle 170 coupled proximally thereto. The proximal handle 160 of the inner shaft 108 is disposed proximally to the proximal handle 170 of the outer shaft 102, and the proximal handle 160 is configured to be rotated independently of movements of the outer shaft 102. It should be appreciated that the proximal handles 160, 170 are shown by way of example only, as handles having any suitable configurations, or any other suitable mechanisms, can be coupled to the inner and outer shafts 108, 102. As the inner shaft 108 and the proximal portion 116 of the first anchor body 110 coupled thereto are rotated, the outer shaft 102 remains stationary. Tension is maintained on the terminal end portions 204a, 204b of the suture 204.

During insertion of the suture anchor 106 into the bone hole 212, the bone-engaging features 124 facilitate the engagement of the suture anchor 106 with the wall of the bone hole 212. The suture 204 becomes pinched between the proximal end of the proximal portion 116 of the first anchor body 110, and the edges of the side openings 115a, 115b in the second anchor body 112, and between the proximal end of the proximal portion 116 of the first anchor body 110 and the undersurface of the proximal end of the second anchor body 112.

Figure 8E:
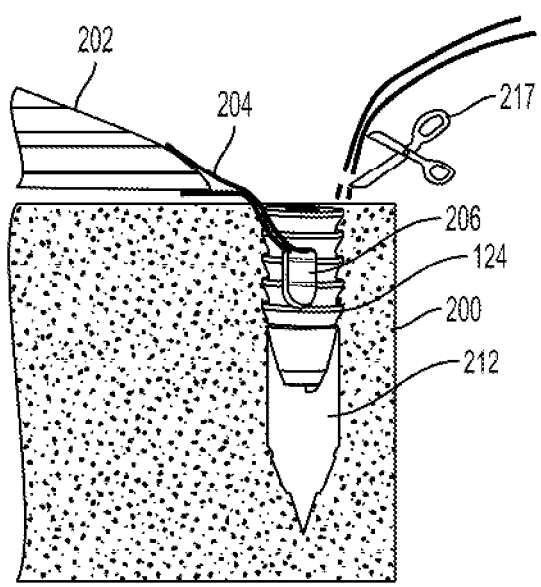
FIG. 8E illustrates the surgical system of FIG. 8D, showing the suture secured.

Once the suture anchor 106 has been inserted into the hole 212 as desired, the inner shaft 108 can be separated from the first anchor body 110, and the outer shaft 102 can be separated from the second anchor body 112. The inner shaft 108 and the outer shaft 102 can be separate components that can be removed separately. For example, the inner shaft 108 can be removed first. Alternatively, in some embodiments, the inner shaft 108 and the outer shaft 102 can be coupled in some manner, while still allowing for independent rotation of the inner shaft 108. FIG. 8E illustrates the suture anchor 106 inserted into the bone, with the inner shaft 108 and the outer shaft 102 removed. FIG. 8E also schematically shows that the terminal end portions of the suture 204 can be trimmed, if desired, such as by using scissors 207. The tissue 202 is thus attached to the bone 200.

The surgical system in accordance with the described embodiments can vary in many suitable ways. For example, the first and second anchor bodies of a suture anchor can have various configurations. Also, a portion of the inner shaft configured to reliably mate with the first, distal anchor body can have various configurations. Other components of the surgical system can vary in different ways as well.

FIGS. 9-13 illustrate another embodiment of a surgical system 300 which operates similarly to the system 100 of FIGS. 1A-8E. Also, the system 300 has similar components to those included in the system 100, and the description of such components is therefore not replicated in connection with FIGS. 9-13.

Figure 9:
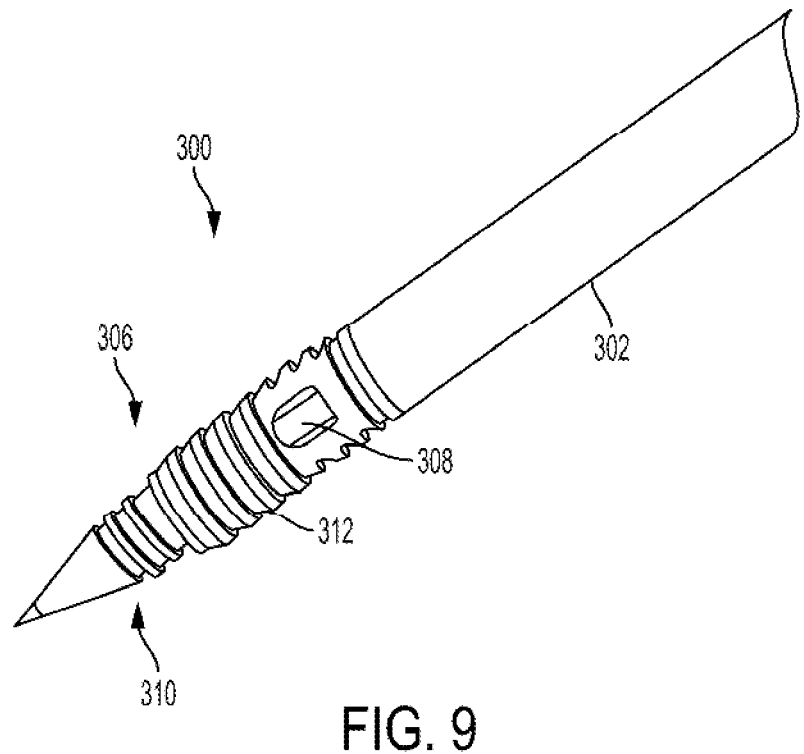
FIG. 9 is a perspective view of another embodiment of a surgical system.
Figure 12:
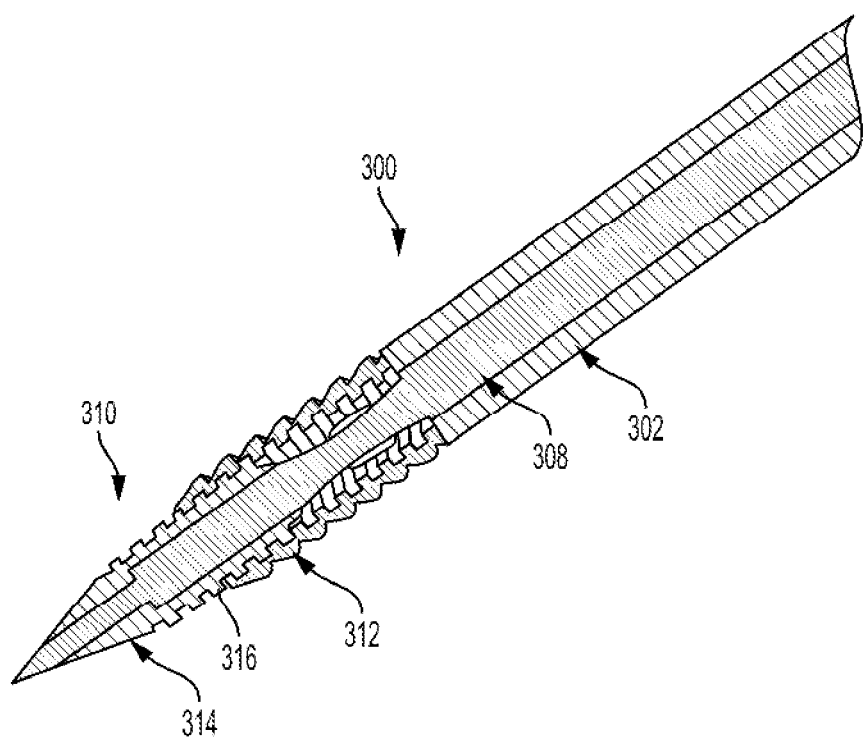
FIG. 12 is a cross-sectional view of the surgical system of FIG. 9.

FIGS. 9 and 12 show that the surgical system 300 includes an outer shaft 302 having a lumen extending therethrough, an implantable anchor assembly having a suture anchor 306, and an elongate awl shaft or inner shaft 308 configured to be removably received within the lumen of the outer shaft 302. The assembly's suture anchor 306 includes a first anchor body 310 and a second anchor body 312 configured such that at least a portion of the first anchor body 310 can be inserted proximally into the second anchor body 312, as discussed in more detail below. The second anchor body 312 is disposed proximally to the first anchor body 310 and has first and second openings 315a, 315b extending through opposed side walls thereof.

Figure 10:
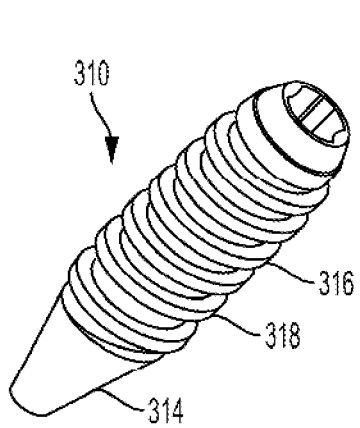
FIG. 10 is a perspective view of a first anchor body of the surgical system of FIG. 9.

In this embodiment, the first anchor body 310 has a distal portion 314 and a proximal portion 316 having an external thread 318 formed thereon that is configured to mate with a corresponding thread formed in the lumen of the second anchor body 312. As shown in FIGS. 10 and 12, the distal portion 314 is distally tapered and its proximal end from which the proximal portion 316 extends has an outer diameter that is approximately the same as an outer diameter of the proximal portion 316. In this embodiment, a lumen extending through the first anchor body 310 does not have a lock/key-type inner feature, and the inner shaft 108 can frictionally or otherwise engage the lumen of the first anchor body 310.

Figure 11:
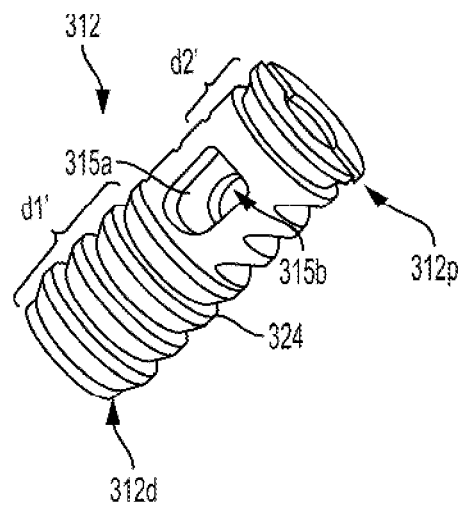
FIG. 11 is a perspective view of a second anchor body of the surgical system of FIG. 9.

The second anchor body 312 has bone-engaging features, such as ribs 324, formed thereon. The openings 315a, 315b extend through opposed side walls of the second anchor body 312 at positions offset from the proximal and distal ends 312p, 312d thereof. In this example, as shown in FIG. 11, each of the openings 315a, 315b is formed such that its distal end is offset from the distal end 312d of the second anchor body 312 at a first distance d1' that is greater than a second distance d2' between the proximal end 312p of the second anchor body 312 and a proximal end of the opening. When the proximal portion 316 of the first anchor body 310 is inserted into the lumen of the second anchor body 312, the openings 315a, 315b are occluded so as to pinch a suture between the inner wall of the second anchor body 312 and the outer wall of the first anchor body 310.

Figure 13:
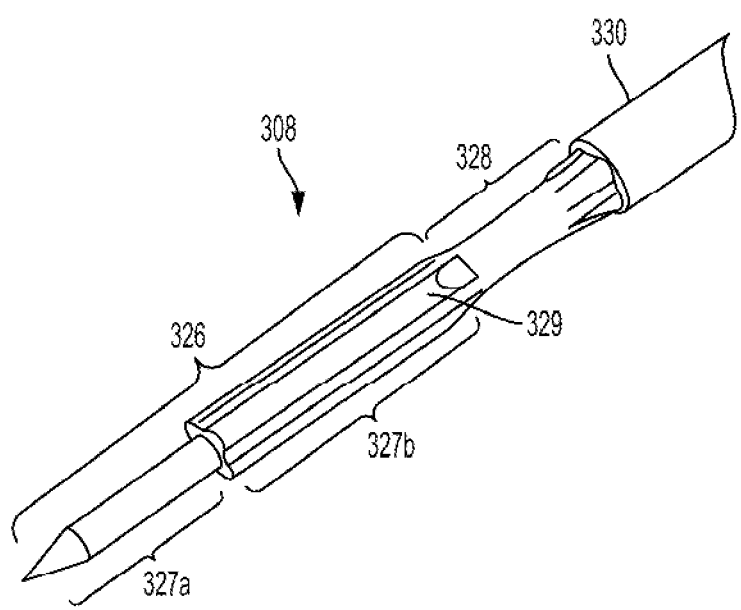
FIG. 13 is a perspective view of an inner shaft of the surgical system of FIG. 9.

As shown in FIG. 13, the inner shaft 108 has a distal driver shaft portion 326 terminating at the shaft's distal end 108d, an intermediate portion 328, and a proximal portion 330. The driver shaft portion 326, which is configured to be removably coupled to the first anchor body 310, has a distal portion 327a and a proximal portion 327b. The proximal portion 327b has longitudinal protrusions 329 formed thereon, as shown in FIG. 13 (or other suitable surface features can be formed) that are configured to be removably coupled to the first anchor body 310 within the inner lumen of the first anchor body 310. The distal portion 327a of the driver shaft portion 326 has a smaller outer diameter than the proximal portion 327b and has a substantially circular cross-section. In the assembled configuration, the distal portion 327a of the driver shaft portion 326 extends through the distal portion 314 of the first anchor body 310. The driver shaft portion 326 of the inner shaft 108 can be frictionally or otherwise engaged with the lumen of the first anchor body 310. The system 300 can be used to attach soft tissue to bone similar to the way in which the system 100 can be used, as discussed above in connection with FIGS. 8A-8E.

Figure 14:
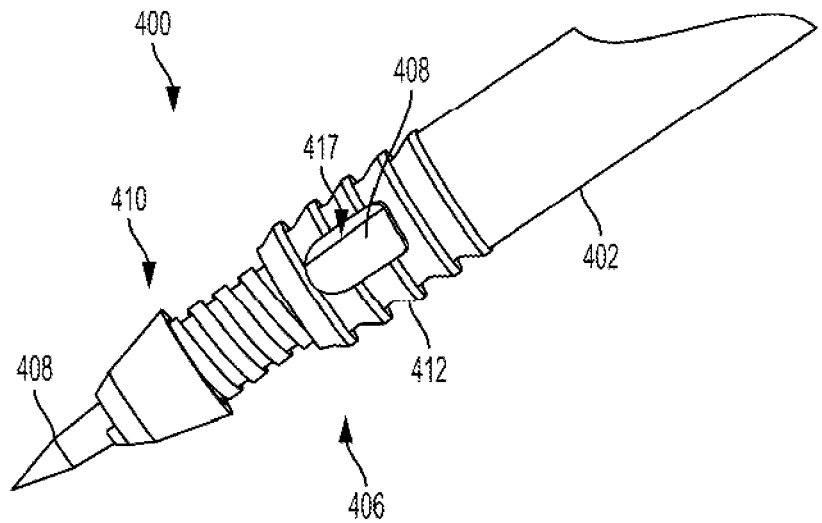
FIG. 14 is a perspective view of another embodiment of a surgical system.
Figure 15:
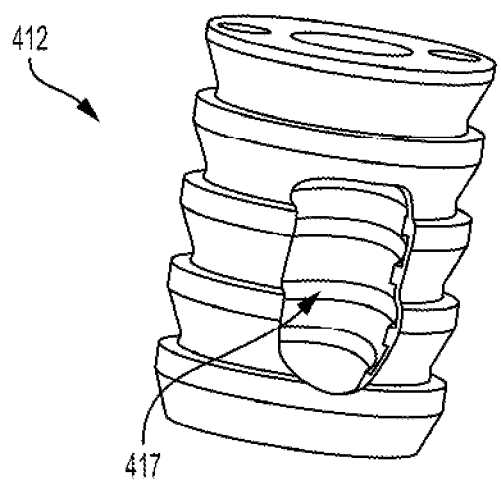
FIG. 15 is a perspective view of a second anchor body of the surgical system of FIG. 14.

In some embodiments, as mentioned above, one opening can be is formed through a side wall of a second anchor body of the suture anchor. The single opening can be formed similar to one of the first and second openings 115a, 115b. FIG. 14 illustrates an example of a surgical system 400 that can be similar to surgical system 100 of FIGS. 1A-8E, and the description of components of the system 400 is therefore not replicated herein. As shown in FIG. 14, the surgical system 400 includes an outer shaft 402, an implantable anchor assembly including a suture anchor 106, and an elongate awl shaft or inner shaft 408 configured to be removably received within a lumen 104 of the outer shaft 402. Similar to suture anchor 106 of system 100 (FIG. 1A), the suture anchor 406 includes a first anchor body 410 and a second anchor body 412 configured such that at least a portion of the first anchor body 410 can be inserted proximally into the second anchor body 412. The second anchor body 412 is disposed proximally to the first anchor body 410, and the second anchor body 412 has an opening 417 extending through a side wall thereof. FIG. 15 illustrates the second anchor body 412 having the opening 417.

Figure 16:
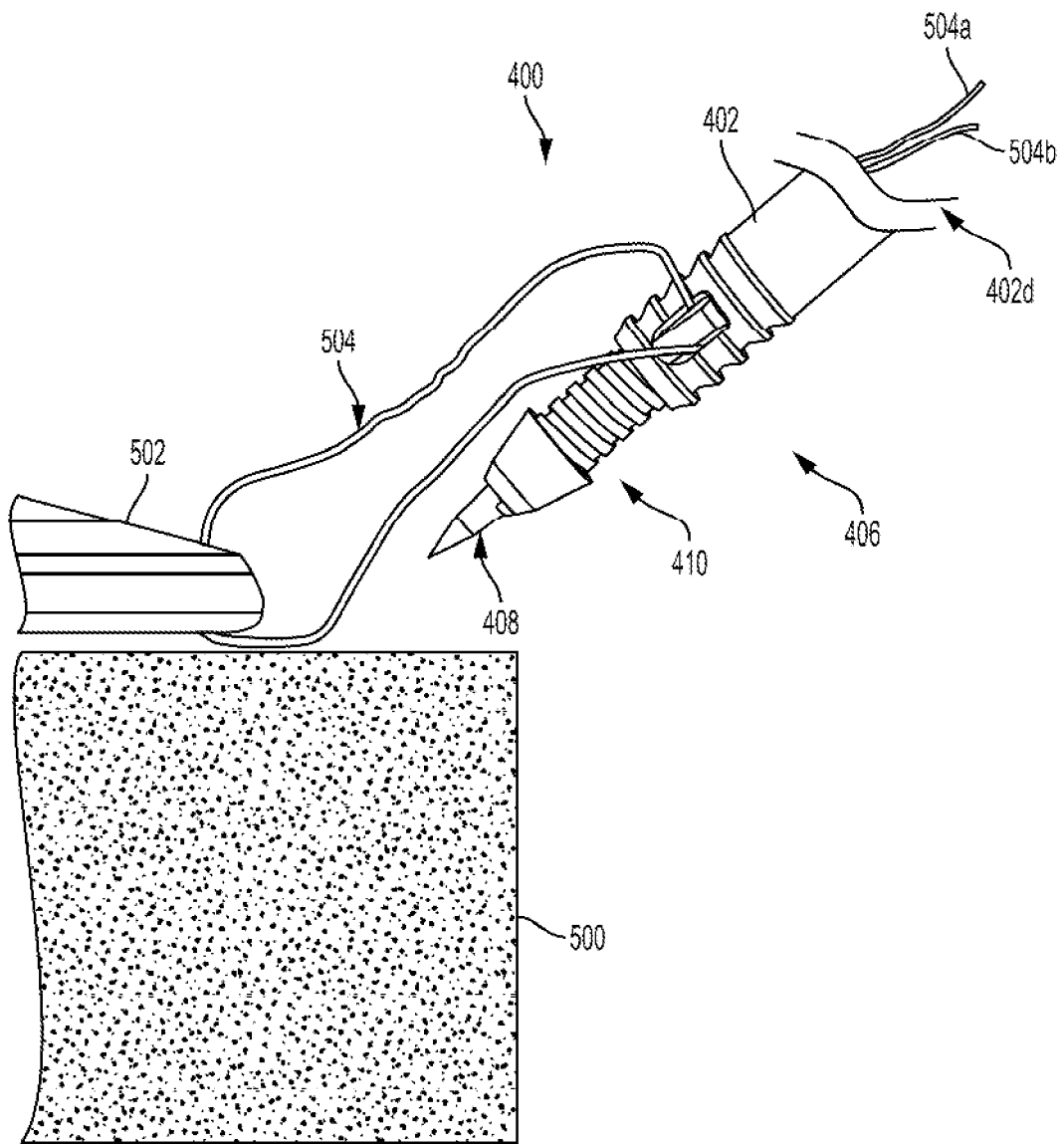
FIG. 16 illustrates the surgical system of FIG. 14, showing a suture coupled to the system, and the system delivered to a bone.

The system 400 can be used in a method for performing a surgical repair, to (re) attach tissue to bone similar to the manner in which the surgical system 100 can be used, as discussed above in connection with FIGS. 8A-8E. However, because the single opening 417 is formed in the second anchor body 412, a suture can extend through the opening such that terminal end portions thereof extend proximally through a lumen of the outer shaft 402. Thus, FIG. 16 illustrates bone 500 and soft tissue 502 (e.g., a tendon) that is to be attached to the bone 500 using the surgical system 400. As shown, a suture 504 is coupled to the tissue 502, such as by being passed through and/or wrapped around tissue 502. As shown in FIG. 16, terminal end portions 504a, 504b of the suture 504 are passed through the second anchor body 412 such that the terminal end portions 406a, 406b extend through the opening 417 extending through a side wall of the second anchor body 412 and communicating with a lumen in the second anchor body 412. The terminal end portions 504a, 504b of the suture 504 can be passed through the opening 417, through a lumen of the outer shaft 402 (e.g., a lumen that is similar to lumen 104 of the outer shaft 102 in FIG. 1A), and the terminal end portions 504a, 504b of the suture 504 can extend from a proximal end 402 of the outer shaft 402, schematically shown in FIG. 16. In use, the suture 504 can be tensioned similar to suture 204 of FIGS. 8A-8E. Other steps of the method for performing a surgical repair using the system 400 can be performed similar to the manner in which the surgical system 100 can be used, as discussed above in connection with FIGS. 8A-8E.

The described systems and methods provide certain advantages. For example, among the advantages is the ease with which the repair technique can be performed to securely attach soft tissue to bone without the need to tie knots. The described techniques allow tensioning sutures separately from the insertion of a suture anchor into bone. Another advantage is that the anchor is inserted into the bone using an awl shaft (e.g., inner shaft 108 or 308), and no additional instrument is required to initiate a bone hole.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device, e.g., the shafts, can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the components of the system described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred the components are sterilized. This can be done by any number of ways known to those skilled in the art including beta or gamma radiation, ethylene oxide, steam, and a liquid bath (e.g., cold soak).

One skilled in the art will appreciate further features and advantages of the described subject matter based on the above-described embodiments. Accordingly, the present disclosure is not to be limited by what has been particularly shown and described, except as indicated by the appended claims. All publications and references cited herein are expressly incorporated herein by reference in their entirety.

What is claimed is:

1. A surgical method, comprising:
    initiating a hole in bone with a distal tip of an elongate shaft extending through a first lumen of a first anchor body and through a second lumen of a second anchor body that is located proximal to the first anchor body along a length of the elongate shaft;
    advancing the first anchor body into the hole in bone, thereby widening the hole, followed by advancing the second anchor body into the hole such that the second anchor body is located in the hole proximal to the first anchor body; and
    with the first anchor body in the hole and with the second anchor body in the hole proximal to the first anchor body, rotating the elongate shaft, thereby causing the first anchor body to move proximally into the second lumen of the second anchor body.

2. The method of claim 1, wherein the second anchor body has an opening formed through a side wall thereof that becomes occluded when the first anchor body moves proximally into the second lumen of the second anchor body.

3. The method of claim 2, wherein a suture extends through the opening; and
    the first anchor body moving proximally into the second lumen of the second anchor body causes the suture to be secured between a wall of the hole and an outer surface of the second anchor body.

4. The method of claim 3, wherein the first anchor body moving proximally into the second lumen of the second anchor body also causes the suture to be secured between an inner wall of the second anchor body and an outer wall of the first anchor body.

5. The method of claim 3, further comprising tensioning the suture, thereby bringing a tissue coupled to the suture closer to the hole.

6. The method of claim 1, wherein the first anchor body has a distal dilator feature that widens the hole as the first anchor body is advanced into the hole in bone.

7. As assembly method, comprising:
mating a proximal end of a first anchor body and a distal end of a second anchor body;
receiving an inner shaft within a lumen of an outer shaft;
receiving the inner shaft through the first and second anchor bodies such that a distal end of the inner shaft protrudes beyond a distal end of the first anchor body; and
mating a proximal mating feature of the second anchor body and a distal mating feature of the outer shaft;
wherein the inner shaft is configured to advance the first and second anchor bodies into bone; and
wherein after the first and second anchor bodies have been advanced into the bone, the inner shaft is configured to rotate and thereby cause the first anchor body to move proximally relative to the second anchor body.

8. The method of claim 7, further comprising mating a first mating feature of the inner shaft with a second mating feature of the first anchor body;
wherein the first mating feature is on an exterior surface of the inner shaft, and the second mating feature is within a lumen of the first anchor body.

9. The method of claim 8, wherein the first mating feature enters the lumen of the first anchor body through a key-hole of the first anchor body that extends distally into the lumen of the first anchor body towards the second mating feature of the first anchor body.

10. The method of claim 9, wherein the mating of the first and second mating features reversibly locks the inner shaft within the lumen of the first anchor body so as to allow the inner shaft to rotate and thereby cause the first anchor body to move proximally relative to the second anchor body.

11. The method of claim 7, wherein one of the proximal and distal mating features includes a male mating feature, and the other one of the proximal and distal mating features includes a female mating feature.

12. The method of claim 7, wherein the proximal mating feature is mated with the distal mating feature such that a proximal surface of the second anchor body abuts a distal surface of the outer shaft.

13. The method of claim 7, wherein with the proximal end of the first anchor body and the distal end of the second anchor body mated, the inner shaft received through the first and second anchor bodies, the inner shaft received within the lumen of the outer shaft, and the proximal mating feature of the second anchor body and a distal mating feature of the outer shaft mated,
the distal end of the inner shaft is configured to initiate a hole in the bone,
the inner shaft is configured to advance the first and second anchor bodies into the hole in the bone, and
the inner shaft is configured to rotate and thereby cause the first anchor body to move proximally relative to the second anchor body.

\* \* \* \* \*